United States Patent
Chechersky et al.

[11] Patent Number: 6,030,343
[45] Date of Patent: Feb. 29, 2000

[54] SINGLE BEAM TONE BURST ULTRASONIC NON CONTACT TONOMETER AND METHOD OF MEASURING INTRAOCULAR PRESSURE

[75] Inventors: Vladimir Chechersky, Ardmore; Peter George Gross, Bala Cynwyd, both of Pa.

[73] Assignee: PGVC LP, Bryn Mawr, Pa.

[21] Appl. No.: 08/923,052

[22] Filed: Sep. 3, 1997

[51] Int. Cl.[7] ........................................... A61B 3/16

[52] U.S. Cl. ................. 600/399; 600/405; 600/561; 351/208

[58] Field of Search ................... 600/398, 399, 600/400, 402, 405, 561; 351/208, 212

[56] References Cited

U.S. PATENT DOCUMENTS

| | | | |
|---|---|---|---|
| 4,886,066 | 12/1989 | Ingalz et al. | 128/645 |
| 4,928,697 | 5/1990 | Hsu | 600/402 |
| 4,930,507 | 6/1990 | Krasnicki | 128/649 |
| 4,945,913 | 8/1990 | Krasnicki | 128/649 |
| 5,148,807 | 9/1992 | Hsu | 128/649 |
| 5,251,627 | 10/1993 | Morris | 600/398 |
| 5,396,888 | 3/1995 | Massie | 128/649 |
| 5,636,635 | 6/1997 | Massie et al. | 600/405 |

*Primary Examiner*—Cary O'Connor
*Assistant Examiner*—Charles Marmor, II

[57] ABSTRACT

An ultrasonic, non-contact tonometer for measuring the intraocular pressure (IOP) of an eye utilizing a single ultrasonic beam of appropriate frequency and power which simultaneously accomplishes both an ocular deformation and its measurement is provided comprising an ultrasonic transducer assembly, utilizing either a traditional head rest or a goggle-type adapter for precisely reproducible positioning of the transducer assembly relative to the eye allowing for distance and alignment adjustments, and an electronic section for signal processing, quality of precision monitoring and for the direct display of the IOP reading. A process for IOP measurement comprising the steps of continually tracking a reference phase shift between the incident and reflected beams while the instrument is in a continuous-wave low-power mode, powering up the incident beam to produce a short tone burst (amplitude surge) carrying an acoustic pressure to deform the eye and measuring the change in the phase shift of the reflected beam caused by the deformation is also provided.

16 Claims, 7 Drawing Sheets

SINGLE BEAM TONE BURST ULTRASONIC NON CONTACT TONOMETER AND METHOD OF MEASURING INTRAOCULAR PRESSURE

FIELD OF INVENTION

This invention relates to the examination of the eye and, in particular, tonometers and tonometric procedures to measure intraocular pressure (IOP).

BACKGROUND OF THE INVENTION

Clinical instruments for IOP measurements are referred to as ophthalmic tonometers or just tonometers. Tonometric procedures are based on creating a deformation of the cornea with a known external force and then relating the extent of the deformation to the IOP with appropriate previously obtained calibrations using enucleated eyes or model eyes. Deformations have been historically grouped into indentations and applanations; the latter are deformations of lesser extent in the volume of ocular fluid being displaced and therefore cause a smaller amount of stretching in the ocular coats (sclera and cornea), which stretching causes inaccuracies in the IOP determinations and is referred to as ocular rigidity. A brief history of tonometers actually in use at some point in time, can be found in textbooks or review articles (e.g., Craven, E. R., Shields, R. L.: "Tonometry in Clinical Practice", in the *Glaucoma Series*, ed.: Starita, R. J., *Clinical Signs in Ophthalmology*, vol XII, no.1, Mosby-Year Book, Inc., 1990).

The contact tonometer most widely used at the present time is the applanation tonometry devised by H. Goldmann (U.S. Pat. No. 3,070,997) in which the cornea is flattened by a device having a plane contact surface; in it the force necessary to achieve a standardized applanation 3.06 mm in diameter is calibrated to provide the IOP. For a typical cornea having a radius of curvature of 8 mm this corresponds to a central flattening of dX=0.15 mm; the corresponding volume of the displaced intraocular fluid is about $0.2\,\mu l$ or approximately $3\times10^{-5}$ of the entire intraocular fluid volume and is achieved typically with a force of only 1 to 2 g.

The Goldmann applanation and other contact-type tonometers suffer from a number of shortcomings. Their use requires the cornea to be prepared by applying a topical anesthetic to minimize patient's discomfort. This, however, increases the risk of eye damage because the patient's sensitivity to normal pain is depressed. Further, any contact with the corneal tissue carries the risk of infection and corneal abrasion. The results of measurements depend on the analysis of deformation produced by mechanical contact with the cornea which necessitates that the morphology of the cornea be close to an ideal condition; however, this is not the case in many corneas altered by pathologic conditions, thereby precluding the use of Goldmann tonometry. Finally, the accuracy is adversely affected by size variations of eyes and by stiffness variations of the cornea and sclera, uncontrolled movement of the patient's head and eyelids, and the cardiac and pulmonary cycles registered through the corneal surface. Accordingly, these instruments require great skill in order to provide safe and accurate measurements and must be used either by a physician or a well-trained clinical technician.

The most widely used non-contact tonometer at the present time is the air puff instrument originally introduced by Grolman in the 1960's (U.S. Pat. No. 3,538,754). In this type of tonometer, a pulse of compressed air is directed at the cornea which will be deformed from convex to flat and then to concave following the increasing pressure of air; an optical system identifies, in time, the applanation event and, being synchronized with the air puff source, can indicate the IOP. Several improvements of the Grolman air puff tonometer have also been patented. While the air puff type tonometers have eliminated both the need for the topical anesthesia and contact with the eye, they are expensive, bulky, show a gradual decrease in accuracy with increasing pressure to be measured, difficulties with alignment while the audible sound and strong surge of air hitting the surface of the cornea cause patient apprehension and discomfort.

Several designs of contemporary tonometers disclosed in numerous U.S. patents issued in the 1980's and 1990's utilize different techniques based on combinations of sound, ultrasound, optics, and electronics.

U.S. Pat. No. 5,396,888 issued in 1995 to N. Massie and B. Maxfield discloses a combination of multiple ultrasonic sources with optical devices in an attempt to create an improved tonometer. That tonometer is based on an analysis of the deformation of the cornea caused by a known external force. The use of ultrasound by the '888 patent to generate the force applied to the eye has definite advantages over air-puff tonometry where compressed air is used. To increase the accuracy of the IOP measurements, this patent discloses ultrasound power generation, measuring and ranging transducers, a visualization system to provide an image of the eye for the clinician, applanation and indentation sensors, and a transverse alignment indication and detection system. In addition, to reduce the sensitivity of the instrument to various sources of electromagnetic interference and to the patient's head and/or eye movements, complex phase sensitive modulation-demodulation techniques were incorporated. These highly complex and expensive additions restrict the potential use of such an instrument to clinics, hospitals and research laboratories.

The complexity and numerous shortcomings of non-contact tonometers proposed so far are part of the reasons why they have not found a real commercial use and even routine eye pressure checkups still involve expensive contact equipment, requiring topical anesthesia and specially skilled persons (usually a physician) to be used safely and accurately.

Since the most important application of ophthalmic tonometry is its use for preventive or early detection of glaucoma and for conducting the ongoing treatment of diagnosed glaucoma by establishing that the IOP stays inside safe limits through regular tonometric monitoring, there is a need for a reliable, accurate, simple-to-use, safe and inexpensive tonometer affordable for daily self-use by any individual at risk for glaucoma.

SUMMARY OF THE INVENTION

The tonometer of the present invention allows an accurate, noninvasive, non-contact quantitative determination of the pressure inside closed deformable systems such as, but not limited to, the IOP inside the human eyeball, utilizing a single ultrasonic beam of appropriate frequency and power, capable of a tone burst (amplitude surge) which simultaneously accomplishes both an ocular deformation and its measurement, comprising of an ultrasonic transducer assembly, utilizing either a traditional head rest or a goggle-type adapter for precisely reproducible positioning of the transducer assembly relative to the eye allowing for distance and alignment adjustments, and an electronic section for signal processing, quality of precision monitoring and for the direct display of the IOP reading.

The method of measuring the internal pressure inside a closed deformable system comprises the steps of continually tracking a reference phase shift between the incident and reflected beams while the instrument is in a continuous-wave low-power mode, of powering up the incident beam to produce a short tone burst (amplitude surge) carrying an acoustic pressure to deform the eye (or other target) and of measuring the change in the phase shift of the reflected beam caused by the deformation which change is thus related to the internal pressure of the target or IOP.

DETAILED DESCRIPTION OF THE INVENTION

The present invention includes the recognition that a single ultrasonic beam of appropriate frequency for transmission through air can be used to track a reference phase shift in the reflected beam, can cause a corneal deformation after appropriate amplitude modulation and that the same beam can precisely detect a change in the reference phase shift in the reflected beam as a result of the deformation, which change in phase shift is thus related to the IOP. Accordingly, the tonometer of the present invention utilizes a single ultrasonic beam to carry both the mechanical energy necessary to deform the cornea and the information about the extent of that deformation which is a measure of the IOP.

Figure 1:
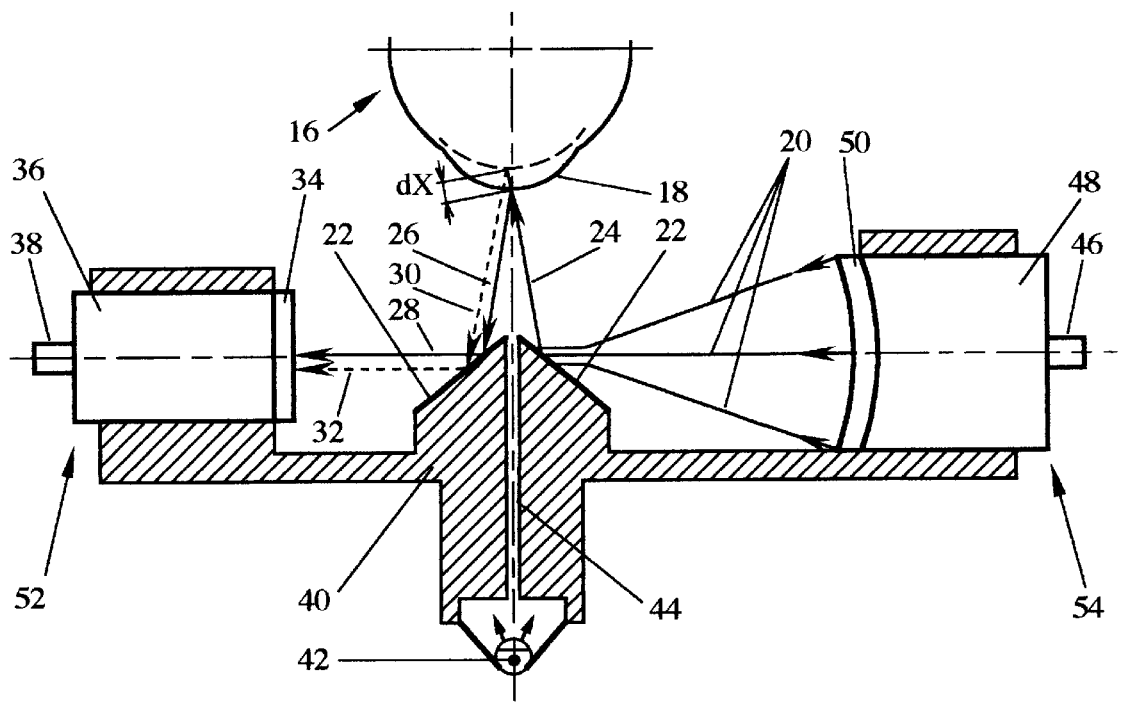
FIG. 1 is a schematic representation of the method showing the two trajectories of the ultrasonic beam, one before and one after the corneal deformation.
Figure 6A:
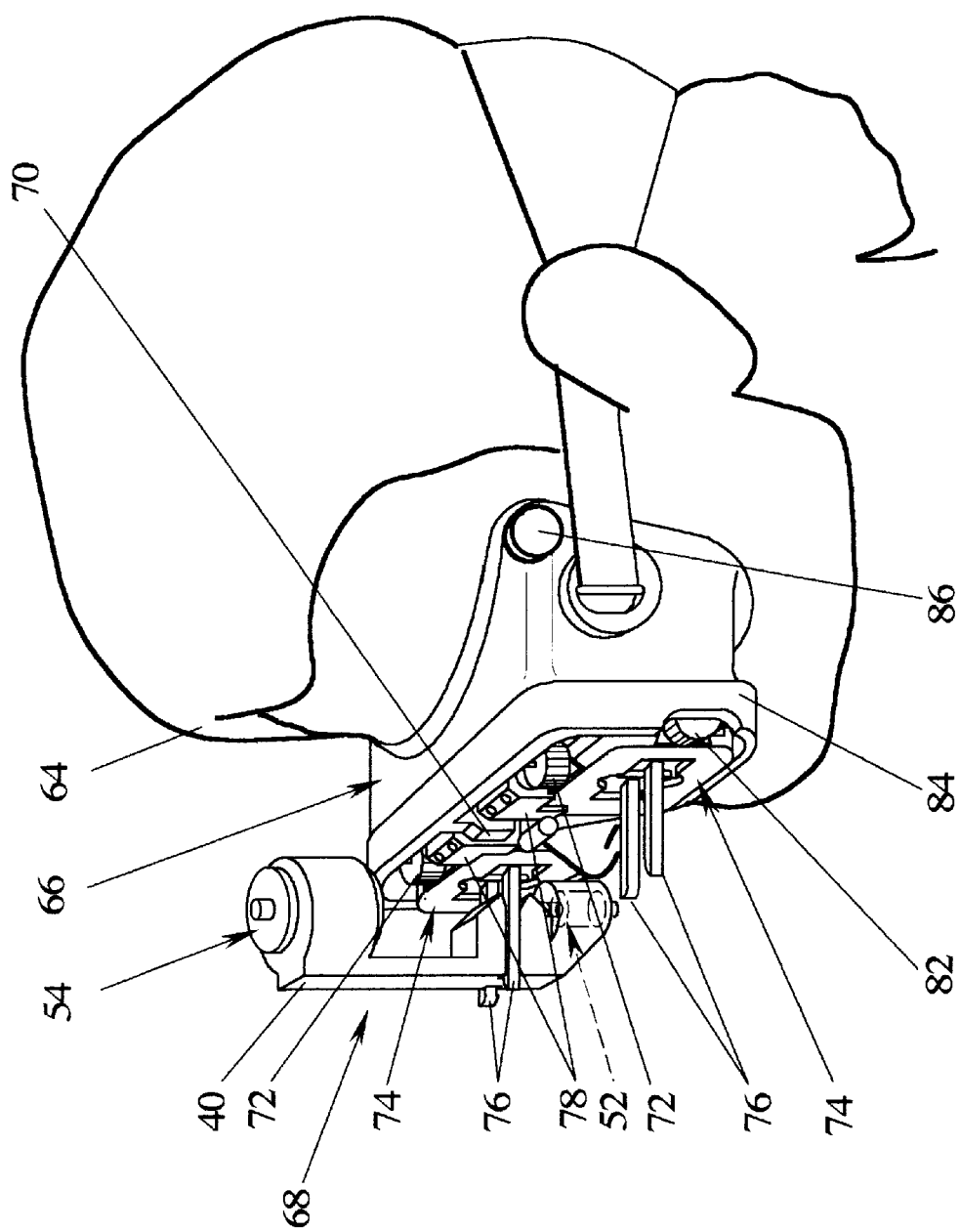
FIG. 6A is an illustrative representation of the positioning of the instrument on the patient's head.
Figure 6C:
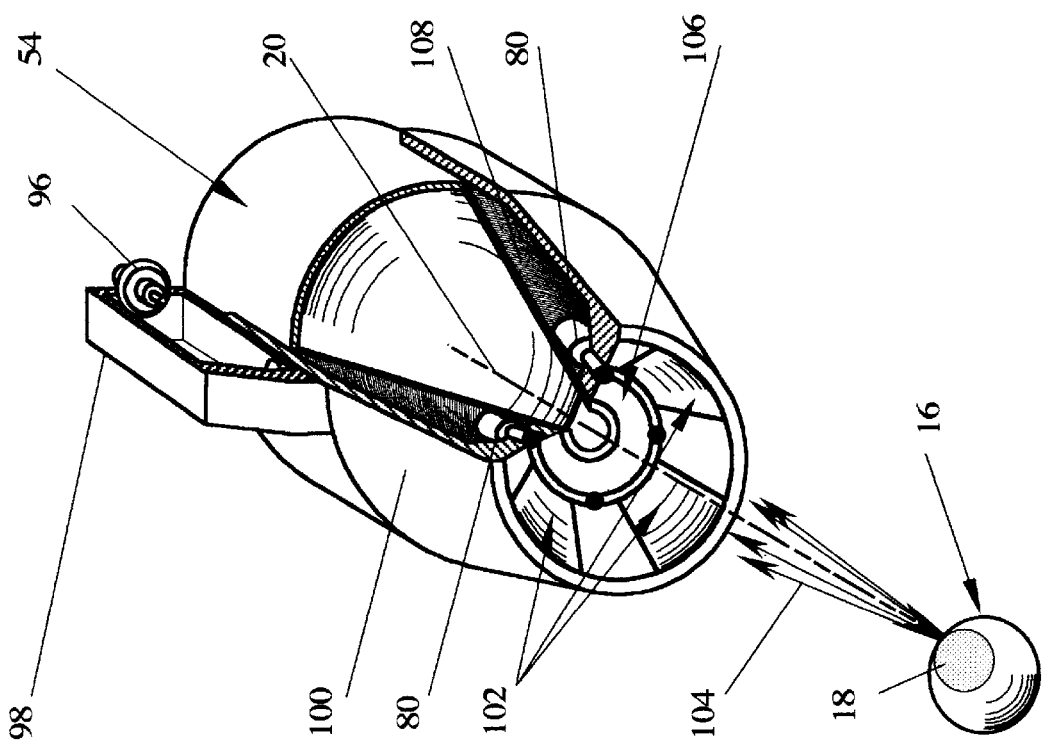
FIG. 6C is a schematic representation of an alternative coaxial design of the transducer assembly.
Figure 6B:
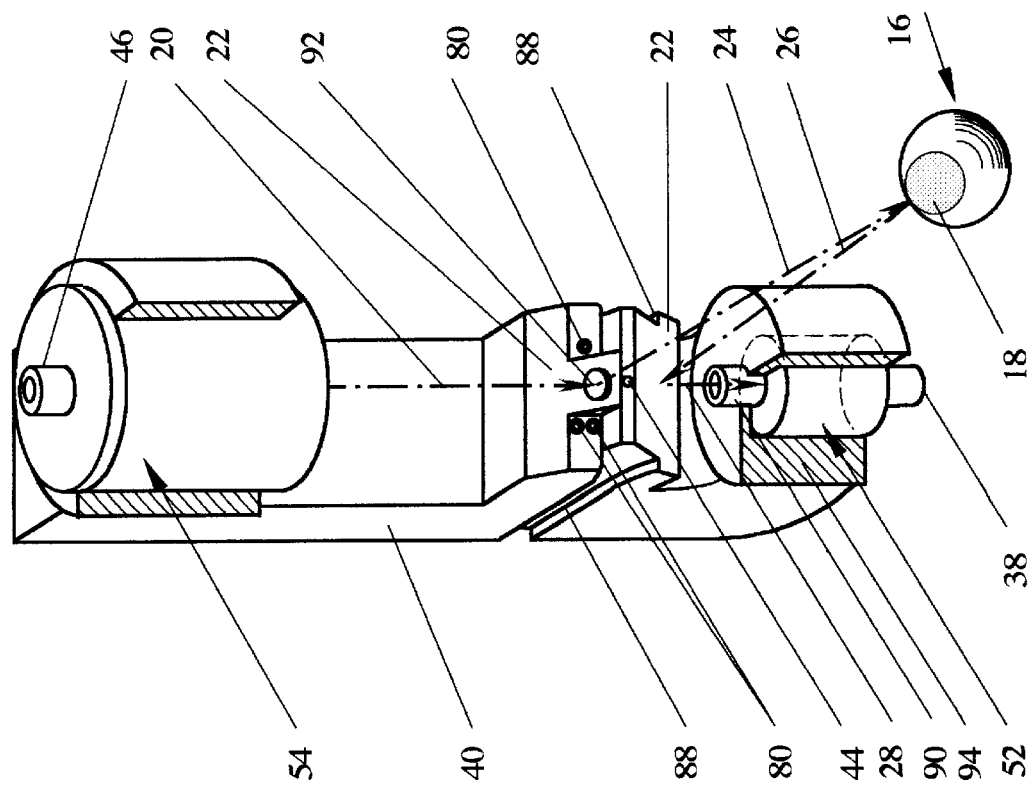
FIG. 6B is a schematic representation of the transducer assembly in preferred embodiment.

A typical embodiment of the present invention is schematically represented by FIG. 1 (see also FIGS. 6A & 6B). A holder 40 provides coaxial positioning for both a housing 48 of a transmitter 54 and a housing 36 of a receiver 52 relative to the opposing sides of reflecting rectangular surfaces 22 which are a part of holder 40. The power transducer 54 transmits a focused high frequency ultrasonic beam 20 toward the proximal reflecting surface 22. The distance between an active surface 50 of transmitter 54 and reflector 22 must be adjusted only once during assembly to obtain maximum reflected signal 24 and depends on the position of the focal plane of the focused source beam. The angle between the two reflecting planes 22 ultimately dictates the distance to the eye 16 in the direction perpendicular to the common axis of the transducers and in the plane of the normals to the two reflecting planes 22; this angle between the reflecting planes 22 is optimal in the range 95–100°. The acoustic pressure component normal to the corneal surface 18 which causes the displacement dX is only slightly reduced (0.5–1.5% for 95–100° angles) and can be corrected for in the measurements. The beam reflected from the cornea 18 can reach an active surface 34 of receiver 52 by two different paths: in the absence of the eye deformation (initial conditions) it will follow along the solid-arrow lines 26, 28; if a deformation dX is produced, it will follow the path shown by the dashed-arrow lines 30, 32. The total path difference between these extreme cases is thus 2dX. This spatial difference causes a phase shift (difference) between incident beam 20 and reflected beam 32. Therefore, one important measurement is the difference between the value of the phase shift $\phi_o$ at the moment preceding the deformation (i.e., phase shift between beam 20 and 28 when they are too weak to cause any deformation dX) and that after beam 20 is suddenly powered up for a short period of time sufficient for indentation dX to occur (i.e., phase shift $\phi_{max}$ between beam 20 and 32). Thus the value $\phi=|\phi_o-\phi_{max}|$ is directly related to the deformation caused by the applied acoustic pressure, and consequently, to the IOP. It is important to understand that this type of phase shift measurement is significantly independent of the static initial conditions (for instance, distance to the eye) or dynamic conditions (for example, miniature eye movements), since the power-up time is too short to be affected by miniature eye movements, and the distance is continuously monitored in the weak-beam state before the power-up occurs. Thus each measurement is instantaneously self calibrated.

There are several special issues important for the proposed new method of the IOP measurement, namely, the preferred frequency range, the power requirements, and the time scale, which are considered as follows.

The frequency of operation affects relative sensitivity $S_o$ of this method which depends on the relation between the round-trip doubling of dX and the half wave length $\lambda/2$ of the ultrasonic beam, i.e., $S_o=4dX/\lambda$. $S_o=1$ corresponds to the 180° phase shift and therefore to the maximum output signal. Ideal dX values should not exceed 50–60 μm (about $\frac{1}{10}^{th}$ of the corneal thickness). The wave lengths $\lambda$ of ultrasonic radiation in 100 KHz–1 MHz frequency range in air are $\lambda$=3300–330 μm. Two important conclusions follow from the above: first, regardless of the chosen frequency, the phase shift will not exceed 180° and therefore can be detected unambiguously by simple electronics; and second, the higher the frequency the better the sensitivity. Further, one has to take into account an attenuation of the ultrasound in air which is strongly frequency dependent and therefore puts certain limits on the practically useful frequency range. A measure of attenuation in air due to absorption is the extinction distance ED, or distance over which the amplitude of a signal is reduced to 1/e of its original value. ED distance in meters can be approximated above 100 kHz by the relation (for 1 ATM air pressure): $ED=5 \cdot 10^{10}/f^2$, where f is the frequency in Hz (R. Hickling, S. P. Marin, "The use of ultrasonics for gauging and proximity sensing in air", J. Acoust. Soc. Am. v.79, No. 4, 1988, pp. 1151–1160). $1f^2$ dependence rapidly reduces the ED from about 5 m at 100 kHz to only 3 mm at 4 MHz. The competition between the frequency dependence of the sensitivity and the attenuation suggests that there is an optimal region of frequencies providing maximum efficiency of the instrument.

Calculation of acoustical absorption in air is based on the equation $p = p_o \exp(-\alpha z)$, where $p_o$ is the RMS pressure amplitude of an acoustical plane wave at a given initial location (for instance, transducer surface), p is the pressure amplitude of the wave after it has progressed a distance z in meters, and $\alpha$ is the absorption coefficient in inverse meters (see above reference to Hickling & Marin). For the sake of simplicity, only the frequency dependence of $\alpha$ will be accounted for. Humidity, and temperature effects become unimportant above about 100 kHz.

From the above equation follows that ED=1/e when $z=1/\alpha$. The frequency dependence of the absorption coefficient is calculated on the basis of the above given high-frequency approximation for the ED so that $\alpha(f)=f^2 \cdot 2 \cdot 10^{-11}$ $m^{-1}$. The frequency-dependent relative sensitivity of the instrument can be written as $S_o(f)=4dX/\lambda$, or $S_o(f)=4dX \cdot f/V$. Finally, an efficiency factor EF of the instrument should be a product of the frequency-and-distance-dependent RMS pressure and the frequency-dependent sensitivity:

$EF = p(f,z) \cdot S_o(f)$.

Adopting the normalization $p_o=1$, $EF = 4\exp(-\alpha z) \cdot dX \cdot f/V$.

Figure 2:
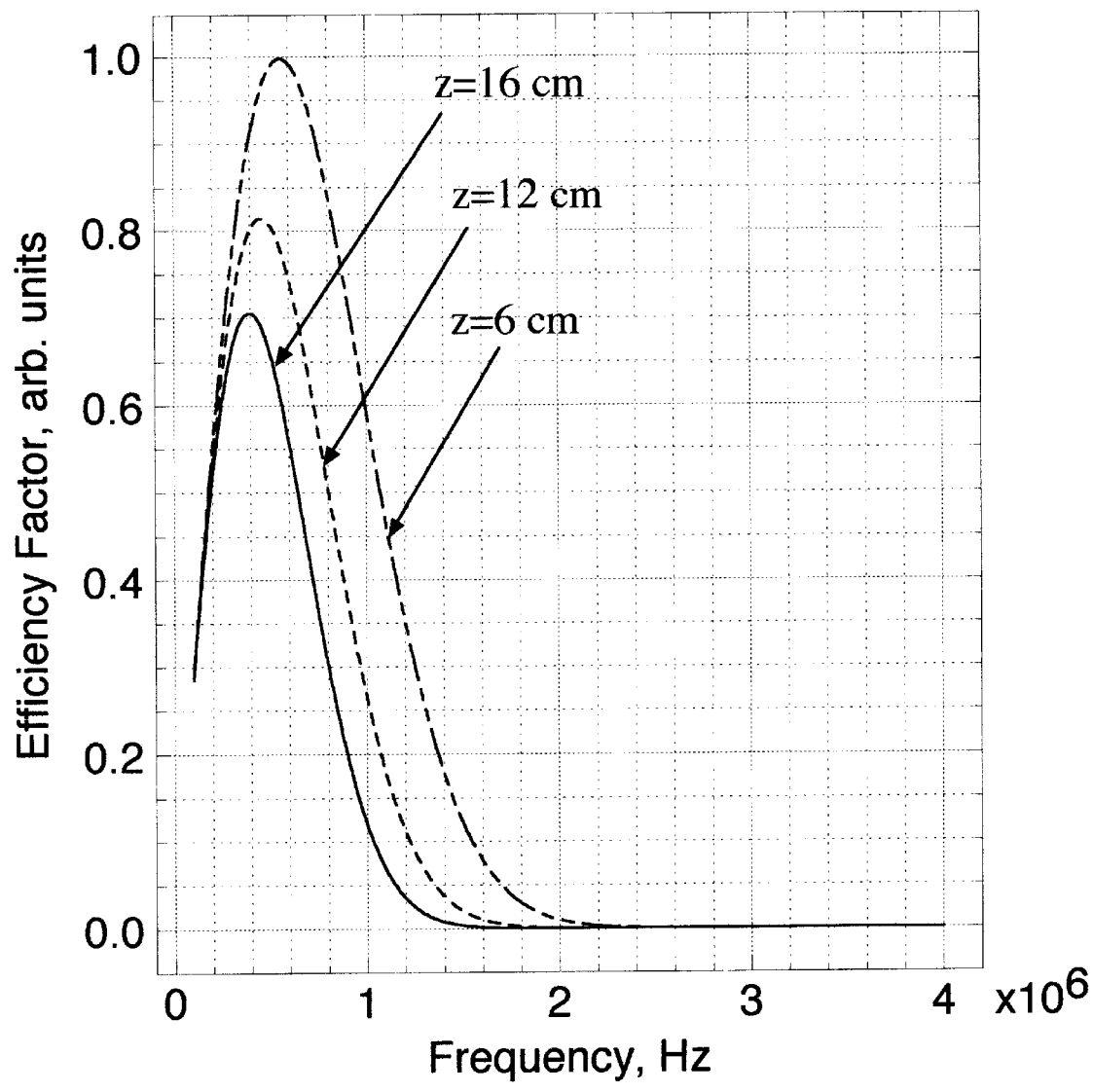
FIG. 2 is a plot of the normalized efficiency of an instrument as a function of the operating frequency and the distance to the eye.

The frequency dependence of the normalized efficiency factor EF for three different z (distance) values is shown in FIG. 2. According to FIG. 2, there is a relatively sharp maximum which moves to the high-frequency side with decrease in the distance. An acceptable efficiency is available in a wide enough range of 0.2–1 MHz depending on the distance allowed by a particular instrument design. FIG. 2 also shows that the preferred frequency range is 200 kHz to 1 MHz. The speed of electronics (in particular, the propagation delay time of a phase detector) will also limit the high frequency end for optimal accuracy.

An estimate of the electric power sufficient for functioning of the tonometer of the present invention is based on the following considerations. In the healthy eye, the intraocular pressure typically ranges from 10 to 20 mmHg [(1.3–2.6) $\cdot 10^3$ N/m$^2$]. In the glaucomatous eye, the IOP is higher and sometimes can jump above 40–50 mmHg [(5.2–6.5)$\cdot 10^3$ N/m$^2$]. In order to produce a corneal deformation, the radiation pressure must have a similar order of magnitude as the IOP to be measured.

The power density W necessary for such an ultrasonic wave can be written as a product of the temporal-average (or RMS) pressure p and the sound velocity V: W=p·V (R. Aston, *Principles of Biomedical Instrumentation and Measurement*, Merrill Pub. Co., 1990, p.504). In the present case of complete reflection due to impedance mismatch, W=0.5p·V because of the momentum conservation law. For the extreme case of $p_{max}=50$ mmHg, taking V=330 m/s in air, we obtain $W_{max}=1.07 \cdot 10^6$ Watt/m$^2$. Thus the acoustic power required to create 50 mmHg pressure on the surface of the cornea using a focused beam with 2 mm diameter in a focal zone (a flat profile is implied) equals to 3.14 Watt. Most recent developments in through-air transducer technology including piezoelectric ceramic-epoxy composite materials and effective matching layers (G. Hayward and A. Gachagan, "An evaluation of 1–3 *connectivity composite transducers for air-coupled ultrasonic applications*", *J. Acoust. Soc. Am.*, v. 99, No. 4, 1996, pp. 2148–2157, and references therein) can achieve an effectiveness of the narrow-band air-coupled transmitter of about 10–15%, i.e., at most 30–45 Watt RMS of electric power is necessary to drive such an instrument. The real power consumption depends on the time required for measurement and will decrease drastically in the tone burst mode of operation.

The tonometer of the present invention can operate in a small deformation mode thereby keeping the influence of corneal and scleral rigidity negligible, because of the very small volume involved in the deformation. As mentioned before, the central value of the depth of the standard deformation created by the Goldmann applanation tonometer is typically dX=0.15 mm. In fact, a much smaller standard deformation can be adopted in the tonometer of the present invention in order to optimize overall accuracy and patient comfort, to minimize power requirements and, perhaps most importantly, to minimize the effects of ocular rigidity on the accuracy of IOP measurements. To provide accuracy and reproducibility of the tone burst method of measurement the ultrasonic beam impinging on the cornea must satisfy certain temporal requirements in order to achieve and maintain an equilibrium deformation dX while acting on a corneal surface area S. The following are three alternative approaches allowing estimate the time scale (duration of a tone burst) of the tonometer of the present invention.

The energy EN necessary to create a small deformation is the product of the IOP times the volume of the small deformation which works out to be EN [Joules]=$1.3 \times 10^{-7} \times$ IOP [mmHg]$\times$dX [mm]$\times$S [mm$^2$] for a cylindrical approximation. To carry an ultrasonic acoustic pressure Pa one needs an ultrasonic beam with acoustic power Wa [Watt]= (3.14/50)$\times$Pa [mmHg]. Thus the time necessary to deliver the acoustic energy equal to the deformation energy is Te [sec]=EN [Joules]/Wa [Watt]=(IOP/Pa)$\times$(S [mm$^2$]/3.14)$\times$dX [mm]$\times 10^{-6}$. For the typical Goldmann deformation above the necessary time Te to deliver the equivalent ultrasonic energy is near $10^{-7}$ sec.

Vibrations of the deformation should dampen to stability in a time Tv that is comparable to the sound travel time through the fluid inside the eyeball; typically, this time is obtained from dividing an average eyeball diameter by the speed of sound in water, or Tv=$25 \times 10^{-3}$ [m]/(1461 m/sec)= $1.7 \times 10^{-5}$ sec.

Given that an external force F suddenly exerts a certain pressure over some corneal area small with respect to the surface area of the eyeball, we want to know the time it takes for F to come into equilibrium with the counteracting force $F_{cf}$ due to the IOP, so that the small deformation of the eyeball created by the constant force F is itself constant as long as the external force persists. Consider a beam delivering acoustic radiation pressure Pa to a corneal surface area S which causes a final deformation dX. The external force acting against the moving element of the cornea is F=Pa·S; the effective mass being moved is a fraction of the displaced mass of aqueous humor (based on well known principles of hydrodynamics which can be applied here but only as an approximation) which can be written as M=S·dX·R·fr, where R is the density of the humor and fr is a fraction less than one in general and here taken to be ¼. Assuming a spring-like IOP-related force in the form $F_{cf}=-KX$, where K is a spring constant, and X is a displacement varying from 0 to dX, and taking into account that at equilibrium, $-F_{cf}=F$ and X=dX, we obtain K=F/dX. The effective force $F_{eff}$ acting on the element of corneal deformation changes with deformation as $F_{eff}=F-F_{cf}=F-F\cdot X/dX=F\cdot(1-X/dX)$; if the acceleration is denoted by A then Newton's law gives us a differential equation for the motion in the form: $A=F_{eff}/M=F\cdot(1-X/dX)/M$, where the effective mass M is treated as a constant for purposes of this approximation; since A is the second time derivative of X, the time-dependent solution of this differential equation with appropriate boundary conditions is just $X=dX(1-\cos(\omega t))$, where $\omega=[F/(MdX)]^{1/2}$. In this approximation we can see that the deformation goes from $X=0$ at time $t=0$ to $X=dX$ at time $t=(3.14/2)/\omega$. For instance, taking the beam diameter to be 2 mm and a Goldmann size deformation $dX=0.15$ mm=150 $\mu$m ($1.5 \times 10^{-4}$ m) gives $S=3.14 \cdot 10^{-6}$ m$^2$ and $M=10^{-6}$ kg, since $R=10^3$ kg/m$^3$. A constant ultrasonic force corresponding to a pressure Pa=10 mmHg acting across a surface S is just $F=P \cdot S=4 \cdot 10^{-3}$ N which results in $t=(3.14/2)(1/\omega)=3\times10^{-4}$ seconds; this is just shorter than the duration of the air puff ($8\times10^{-3}$ seconds) in air puff tonometry, suggesting that our approximate analysis leads us indeed into the appropriate time scale for the deformation equilibrium to be established. This puts the expected upper limit for a typical measurement time under 1 millisecond. This is short enough to avoid pain and damage from being inflicted upon the living eye. Further, it is not limited by the minimum time required to deliver the acoustic energy or to dampen the vibrations.

The tonometer of the present invention can be ideal for small deformations and can be operated in either a fixed-phase-shift-change (analogous to the fixed deformation in Goldmann tonometry) mode or in a fixed-force mode. The fixed-force mode is usable in rapid succession with preprogrammed forces to study the dependence of the deformation on the force, which dependence will be determined by the IOP. The latter mode is still expected to complete a full cycle of measurement in a very short time, since the time required for different degres of small deformations varies as the square root of the extent of the deformation as shown by the expression we obtained for $\omega$ earlier. This preprogrammed force mode is expected to provide important information also about the corneo-scleral rigidity. This can make the present tonometer unique in allowing it to correct for the variation of corneo-scleral rigidity, which varies not only from eye to eye but also from place to place in a given eye.

The short time of measurement allows the required power to stay below about 50 mWatt per measurement; furthermore, only about $10^{-3}$ of the incident power penetrates into the cornea because of near-perfect reflection of ultrasound at the air-cornea interface induced impedance discontinuity.

Advantages of the present invention include the following: A single-beam design requires a minimum of components making an instrument more reliable, small, and simple to use; a tone burst (amplitude surge) mode of operation drastically reduces power consumption making possible battery-powering and enhancing safety considerations; less than $10^{-3}$ sec per measurement guarantees a painless procedure which will not produce any discomfort to the patient, as well as independence of the results of measurement from uncontrollable lower (ordinary) disturbances of any kind, e.g., heartbeat, breathing, eye movements, etc.; a very short time of measurement offers a unique opportunity to study instantaneous IOP changes induced by the different physiological processes in the human body.

Figure 4:
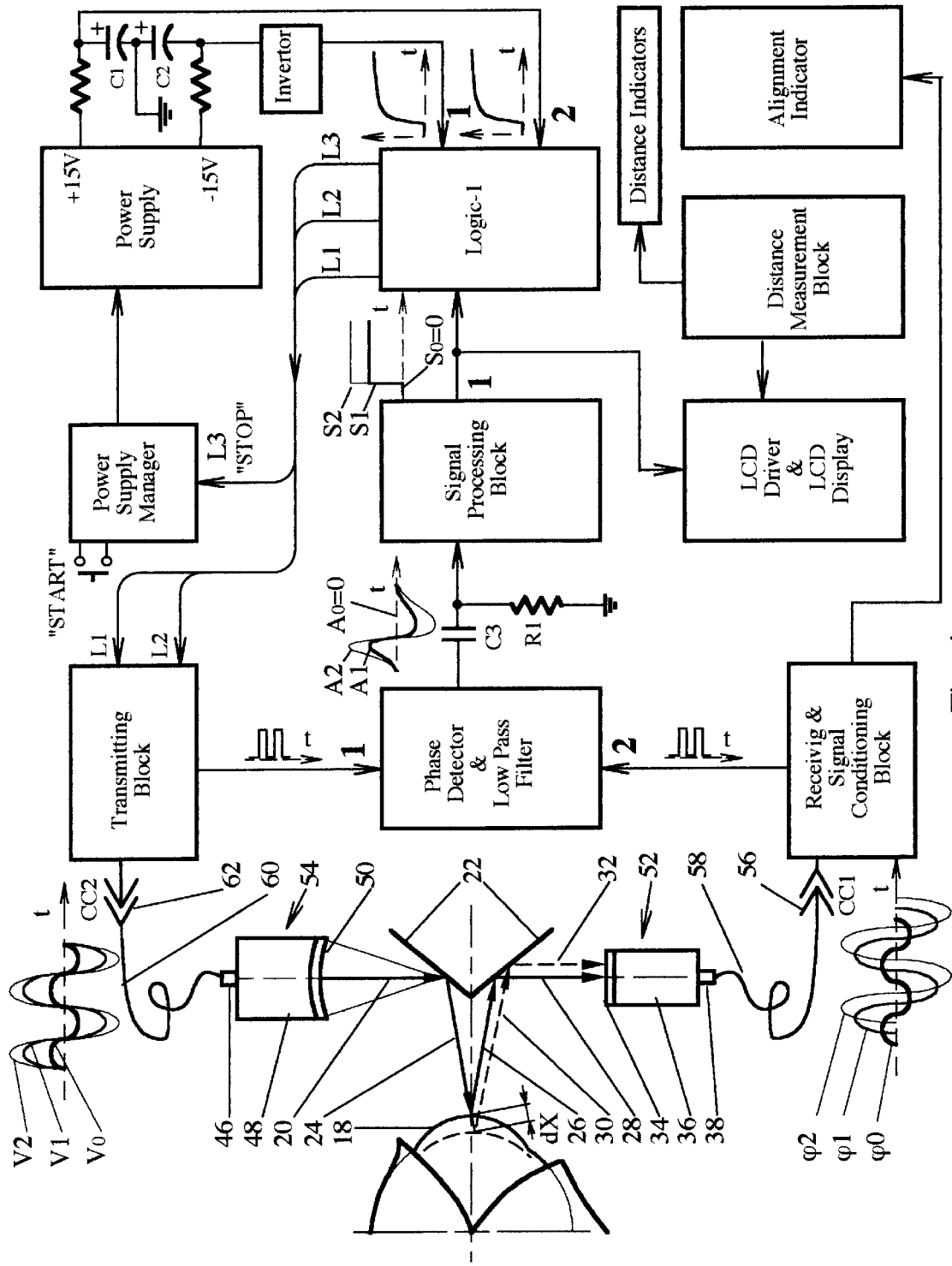
FIG. 4 is a block diagram of a tonometer and displays the logical connections between the electronic component blocks the tonometer comprises.
Figure 5:
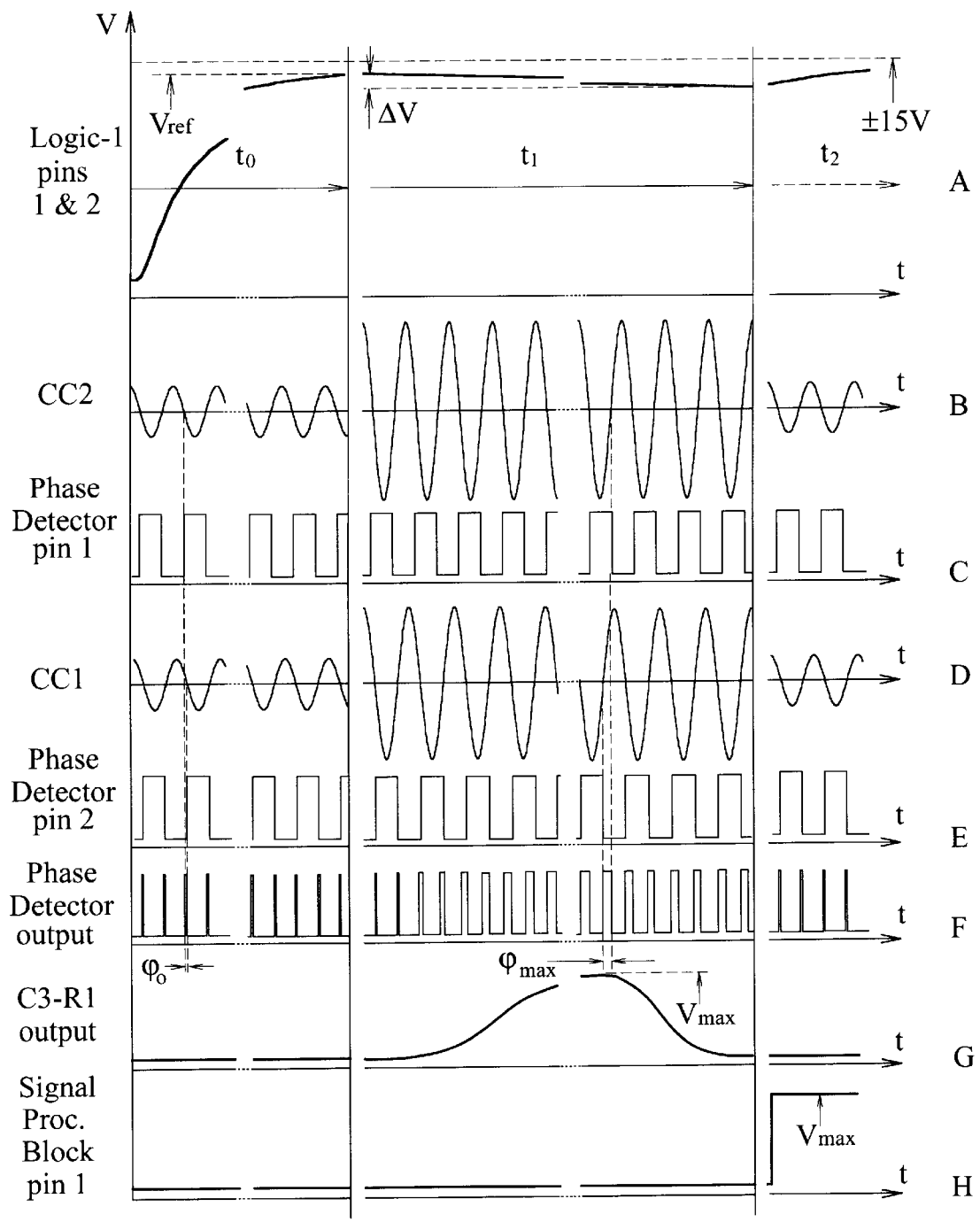
FIG. 5 is a timing diagram for the tonometer of FIG. 4 illustrating shape and phase relations of the signals at key points of the electronic circuitry.

The general principles of operation of the tonometer of this invention can be described as follows. Referring to FIG. 4, the process of measurement is initiated by pushing a "START" button of the "Power Supply Management Block". This provides all electronic circuitry with the necessary voltages. Simultaneously, energy storage capacitors C1 and C2 start to charge as shown in the upper part of FIG. 5. The time to required for the charge of C1 and C2 to reach the predetermined $V_{ref}$ value is chosen to be a few seconds to allow the system to come to equilibrium and the patient to fix the eye. During this time period, "Transmitting Block" of FIG. 4 provides transmitter 54, through coaxial connector 62 (CC2), cable 60 and connector 46, with low-voltage continuous exciting sinusoidal signal $V_o$ which cannot cause any corneal deformation but, being reflected off of the corneal surface, can be reliably detected by the receiving sensor 52 and further processed by the rest of the electronic circuitry. The coaxial connector 38 of sensor 52 is attached to the "Receiving and Signal Conditioning Block" by the cable 58 through a connector 56 (CC1). There is an arbitrary, and therefore unknown, initial phase shift $\phi_o$ between an incident beam 20, 24 and reflected beam 26, 28. These two signals and corresponding phase shift are shown in FIG. 5-(B,$t_o$) and 5-(D,$t_o$) (where our notation has divided FIG. 5 into arrays identified by rows A–H and columns corresponding to time segments $t_0$, $t_1$, $t_2$ so that the relevant panel of FIG. 5 is identified by the specific index pair as just demonstrated). In the receiving and signal conditioning block, the sinusoidal signal is converted into a perfect 50% duty cycle standard rectangular logic signal which carries information exclusively about the phase of the input signal as indicated in FIG. 5-(E,$t_o$). The corresponding stable reference signal initiated from the transmitting block is shown in FIG. 5-(C,$t_o$). These two standardized phase signals are fed into the "Phase Detector & Low Pass Filter Block" of FIG. 4 where they are processed by a phase detector (two input Exclusive OR Gate). Its truth table is such that the output is high ($V_{hi}$) only when inputs are at different logic levels (0&1 or 1&0), so that this relationship implements phase detection by creating an output signal which is essentially a subtraction of the signals in FIG. 5-(C,$t_o$) and FIG. 5-(E,$t_o$) resulting in the signal of FIG. 5-(F,$t_o$) whose frequency is twice that of the input, with a duty cycle depending on the time period when the input signals have an opposite level. From the Exclusive OR Gate type phase detector, there is a linear relationship between the phase angle difference $\phi$ of its inputs and the output signal: $V=V_{hi} \cdot \phi/180°$ (See, for example, J. M. Jacob, *Applications and Design with Analog Integrated Circuits*, Regents/Prentice-Hall, 1993, pp. 325–329). The low pass filter extracts the average value of the digital output of the signal from the phase detector so that the voltage level at the filter output corresponds to the initial phase shift $\phi_o$ between the ultrasonic beams incident upon and reflected by the cornea. A high pass filter C3-R1 (FIG. 4) eliminates an influence of the initial conditions on the final result. Accordingly, at the moment preceding the measurement cycle, the output signal SO of the "Signal Processing Block" in FIG. 4 is equal to zero as shown also in FIG. 5-(G,$t_o$) and 5-(H,$t_o$).

The process of measurement starts at the moment $t=t_o$, when both capacitors C1 and C2 are charged to the $V_{ref}$ value. At that moment, "Logic-1" block 1 in FIG. 4 sends a logic signal L1 to the transmitting block forcing it to increase the driving voltage (V1 in FIG. 4) applied to transmitter 54 as shown in FIG. 5-(B,$t_1$), thus surging in amplitude while keeping the phase of the ultrasonic incident beam unchanged. The duration $t_1$ of this tone burst is determined by the corneal response time already discussed herein and can be adjusted as needed in the logic-1 block. A tone burst causes gradual increase dX of the corneal deformation which reaches its final, equilibrium value in a short time and before the brief tone burst is discontinued. The new phase shift between incident beam 20, 24 and reflected beam 30, 32 follows the deformation caused by the tone burst as depicted in FIG. 5-(B,$t_1$) and FIG. 5-(D,$t_1$). During the tone burst, a time-dependent phase shift between the standard reference signal of FIG. 5-(C,$t_1$) and the standard output signal of the receiving and signal conditioning block of FIG.

5-$(E,t_1)$, being processed by phase detector, produces time-dependent duty cycle at its output as shown in 5-$(F,t_1)$, while the corresponding output of the high pass filter C3-R1 of FIG. 4 is depicted in FIG. 5-$(G,t_1)$. The latter curve reaches its maximum value corresponding to the maximum phase shift $\phi=\phi_{max}$ when the corneal deformation reaches its maximum or final equilibrium value. The peak value $V_{max}$ of this signal is the measure of the intraocular pressure. Actually, the phase changes depicted in FIG. 5 are idealized for clarity of illustration and further analysis makes it obvious that, depending on the initial conditions, in a general case the shape of the output signal of the high pass filter C3-R1 can be similar to that shown in FIG. 4 (A1 or A2). The design of the signal processing block in FIG. 4 is so as to give an output voltage that is always proportional to the degree of deformation (i.e., peak to peak) regardless of the shape of the input signal.

In a time $t=t_1$ the instrument returns to the initial state. To avoid excessive corneal deformation, the power of the first tone burst is minimized for adequate accuracy. An output signal S1 shown in FIG. 4, smaller than the predetermined reference level in the logic-1 block produces the logic signal L2 which forces the transmitter block to increase the power and the cycle of measurements will be repeated (signals V2, A2, and S2 in FIG. 4) at the moment $t_2$ as soon as the charge on C1 and C2 reaches $V_{ref}$ again ($t_2<<t_0$). If the first shot was adequate to obtain a reliable measurement, the logic signal L3 shown in FIG. 4, shuts down the power for all circuits through the power supply manager block. An LCD will directly display the measured pressure since an LCD driver is used in the "reverse reading" mode. In this mode of operation, the displayed reading is inversely proportional to the input voltage. Since the eye pressure-related input signal is also inversely proportional to the pressure, the "reverse mode" of operation of the LCD driver leads to a direct reading of the IOP.

The tonometer of this invention utilizes the same ultrasonic beam which is used for the pressure measurement to accomplish all adjustments required for accurate IOP measurement as described below.

The accurate maintenance and knowledge of the distance between the instrument and the eye is a necessary prerequisite for an accurate IOP measurement. Depending on the particular instrument design, the distance adjustment can be obtained before each measurement or only intermittently to make sure that the adjustment made at the very beginning is maintained within specified limits.

In this invention, the distance control is based on the principle of a "time of flight" measurement and is carried out in a low power mode of operation. The electronic circuitry for this is straight forward state of the electronic art comprising of a crystal clock oscillator, frequency dividers, gating logic, and a digital-to-analog converter (DAC) (designated in FIG. 4 as "Distance Measurement Block"). The digital output can be seen on LCD display; it is also converted into an analog form by a DAC, and finally into three messages: "Too Far", "Too Close", and "OK". Corresponding differently colored LEDs ("Distance Indicators" of FIG. 4) situated in the appropriate place relative to the target eye (see description of FIG. 6B below) give a simple and convenient way for the subject to self-adjust the distance without outside assistance.

The accuracy of distance control depends on the accuracy of the time-of-flight measurement, the accuracy of the speed of sound used to convert time of flight to the distance, and the relation between the radius of curvature of the reflecting surface and the spot size of the beam (see the preceding reference to Hickling and Marin). In the present invention, experience shows that the error of time measurement introduced with a 4-MHz oscillator is about ±0.5 $\mu$sec, or ±0.16 mm; inclusion of a negative temperature coefficient thermistor into an appropriate place of an analog part of the electronic circuitry leads to the elimination of error in the speed of sound due to temperature variations; the distance error for a beam radius of 1 mm and a corneal radius of 8 mm is less than ±0.1 mm or about 0.1% of the total distance.

The focused ultrasonic transducer with a −6 dB focal zone on the order of several tens of millimeters generates a collimated beam having several millimeters depth-of-focus; this allows the accuracy of the eye-to-instrument distance to be relaxed to about ±1 mm without loss of accuracy of the measured IOP.

Figure 3A:
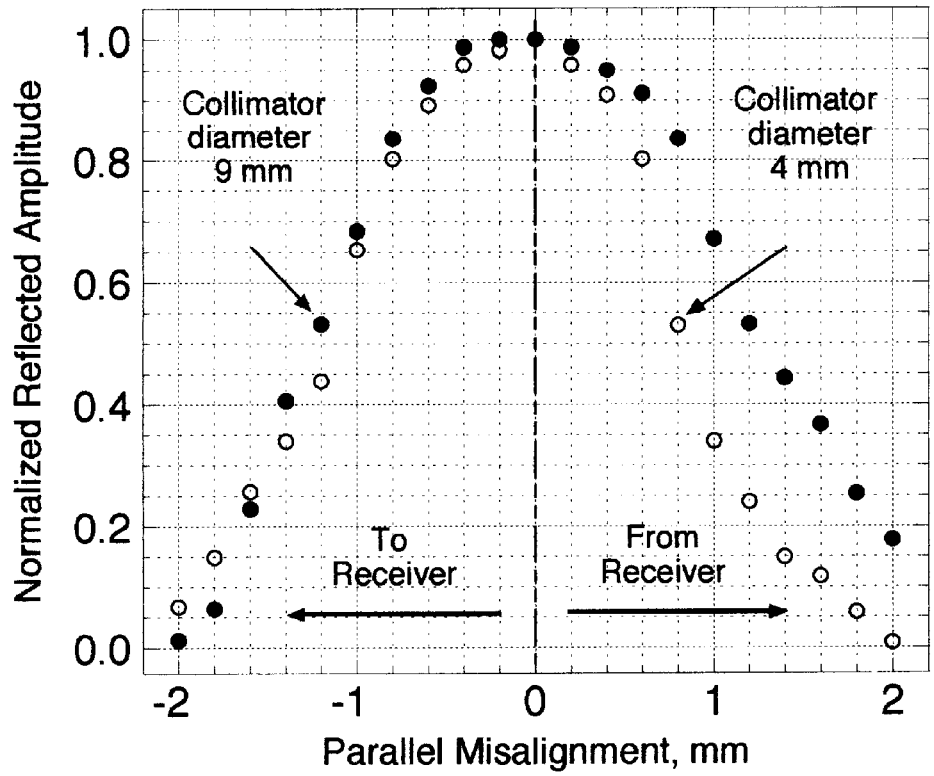
FIG. 3A is an experimental plot showing the sharpness of the alignment for the ultrasonic beam for displacements parallel to the transmitter-receiver axis (see FIG. 1).
Figure 3B:
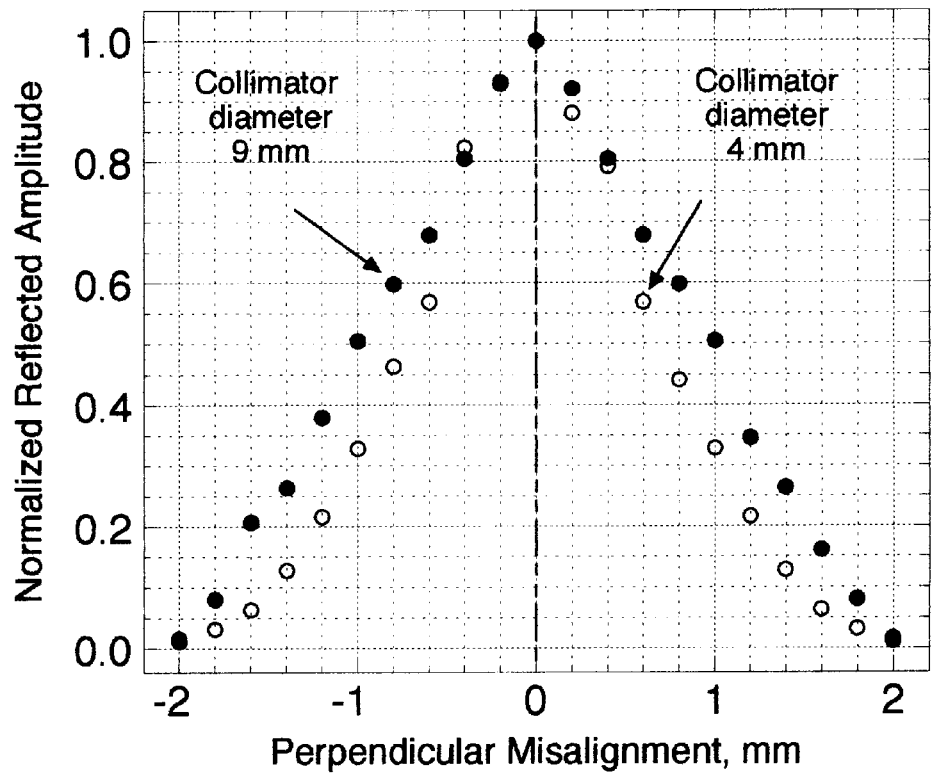
FIG. 3B is an experimental plot showing the sharpness of the alignment for the ultrasonic beam for displacements perpendicular to the plane of the incident and reflected ultrasonic beams (see FIG. 1).

To align the instrument in the plane normal to the visual axis of the eye, a continuous wave (CW) mode of operation in low power regime of unchanged transmitter-receiver arrangement of FIG. 1 is used. One simple alignment procedure uses the specular reflection of ultrasound. Thus, the presence of the cornea, i.e., a sphere of a relatively small radius, in the path of a plane longitudinal wave gives rise to reflection over a range of angles even at the normal incidence. The displacement of the ultrasonic spot in any direction from the apex position at the corneal surface causes strong scattering of the reflected energy which quickly increases with misalignment. The corresponding decrease in the intensity of the reflected beam detected at the receiver is easily analyzed in the electronic circuitry which can control the brightness of a LED accordingly ("Alignment Indicator" in FIG. 4). Since the human eye is very sensitive to the brightness change, especially if the maximum brightness has a moderate value, the accuracy of the alignment can be easily and unambiguously indicated by the brightness of the LED, which can have an adjustable maximum brightness for personal comfort. An experimental plot in FIGS. 3A and 3B illustrates the sharpness of the alignment achievable with this method in the two perpendicular directions within the plane perpendicular to the visual axis. Parallel misalignment corresponds to the displacement along the axis connecting the two transducers in FIG. 1, and perpendicular misalignment means the displacement in the direction normal to this axis. It is possible to get an accuracy of better than ±0.6 mm for the worst case (keeping in mind that the power, i.e. brightness, is proportional to the voltage squared). The accuracy will be significantly enhanced by use of any meter as an indicator of a signal maximum. A LED 42 in FIG. 1 serves as an alignment indicator and navigator relative to the visual axis. Its strongly collimated narrow beam (see FIG. 6B) is also used for an adjustment of the axis 44 of the transducer block 68 (FIG. 6B) coaxially with the visual axis of the eye. LED 42 also provides the patient with a fixating light.

Advanced applications can also be easily achieved with this invention without changing the basic configuration discussed above and shown in FIG. 1. Advanced features include a self-calibration, synchronization of the IOP-measuring event with some physiological event, and a programmable stepwise change of the acoustic pressure allowing corrections of confounding factors affecting the accuracy of the IOP determination such as the stiffness of the cornea and sclera or effects of varying diameters of the eye ball.

Self-calibration helps correct several external factors affecting the sound velocity and the absorption coefficient and, consequently, the generated acoustic pressure and finally, the IOP reading. These factors are the temperature, the humidity, and the atmospheric pressure. On the basis of recently published results (H.E. Bass et al., "Atmospheric absorption of sound: Further developments", J. Acoust. Soc. Am., v. 97, No. 1, 1995, pp. 680–683) one can find, for instance, that the attenuation of 250 kHz sound wave will change in the range 1–1.5% as a result of fluctuations in temperature by ±15° C., atmospheric pressure by ±10%, or humidity of 20–90%. For example, a ±10° C. temperature variation brings about 3.5% change in the sound velocity.

The most effective way to nullify all these potential sources of error is to actually measure the acoustic pressure applied to the eye during each measuring cycle and to normalize the IOP reading accordingly. The present invention utilizes relatively recently introduced ferroelectric polymer polyvinylidene fluoride (PVDF) or its copolymers (see, for example, "*The applications of ferroelectric polymers*", ed. by T. T. Wang, J. M. Herbert, and A. M. Glass, Blackie Ltd., 1988) as a pressure sensor. The thin piezoelectric films of these materials show excellent linearity over a wide range of pressures and a long term stability; they can be easily shaped as necessary and require minimum space. In the design schematically shown in FIG. 1 and in more detail in FIG. 6B the pressure measuring PVDF disc-shaped film should be glued on the surface 22 (from the transmitter side) coaxially with the beam 20 (not shown in FIG. 1), i.e., it must become a part of the reflecting surface. The center of the pressure sensor is located at the focal plane of the transducer, while the distance-transmitter sensor is unchanged. The several corresponding necessary changes in the electronic circuitry are straight forward, the main change being an addition of a multifunction converter microchip (LH0094 from National Semiconductor) used as a precise divider for the normalization of the IOP reading; the signal corresponding to the measured IOP value is fed on the $V_z$ input of the converter while the signal proportional to the acoustic pressure is fed to its $V_x$ input. The converter output is proportional to $(V_z/V_x)$ which, with a cosine correction taking into account an angle of incidence of the ultrasonic beam onto the PVDF sensor surface, is the normalized IOP value cleansed of any external effects (atmospheric and power supply).

External synchronization allows more specific characterization and therefore greater precision of the measurement by taking into account an effect of some physiological event on the measured IOP. Thus, the cardiac pulse produces a pressure pulse in the circulation and a consequent IOP pulse in the eye. With external synchronization included in the electronic circuitry, the IOP measurements can be gated to any phase of the cardiac cycle; this then allows differentiation between the systolic IOP and diastolic IOP which commonly differ by 10% and by much more in certain conditions of cardiac valve insufficiencies. Since the tone burst time scale of operation of the tonometer of this invention is at least two orders of magnitude shorter than the cardiac cycle, external synchronization can provide an accurate IOP cycle which will have significant and new clinical implications. To accomplish such external synchronization the electronic circuitry has to be modified by tapping into either the electrocardiogram or the circulatory pressure pulse or both (see, for example, R. Aston, "*Principles of Biomedical Instrumentation andMeasurement*", Merrill Pub. Comp., Columbus, 1990. pp. 113–134). Preference can be given to the simpler contemporary designs utilizing PVDF films in a compact housing (see, for instance, F. Steenkeste et al., "*An Application of PVF$_2$ to Fetal Phonocardiographic Transducers*", Ferroelectrics, v. 60, 1984, pp. 193–198) suitable to be inserted either into a regular ophthalmologic forehead rest or into a goggle-type instrument configuration shown in FIG. 6A to measure the pulse beats through branches of the external carotid arteries. An addition to the electronics of FIG. 4 includes just one more logic input (not shown) to "Logic-1" block generated by some of the above sensors which, combined with programmable delay, will ultimately dictate the moment of powering up of the incident beam. It is most important to appreciate the fact that the present medical art, which depends on Goldmann tonometry, is unable to differentiate well between values of the IOP cycle and, therefore, the use of the present invention in cardiac-gated mode will define a new and higher medical standard in IOP determination with inestimable potential benefits.

Stepwise change of the acoustic pressure allows one to study the deformation of the cornea as a function of the applied external pressure; such a relationship will be strongly affected by the ocular rigidity as mentioned. This is self evident if one thinks of how much easier it is to deform a basketball than an automobile tire, even when both have equal internal pressures. Extending the electronic circuitry of FIG. 4, which already uses the two or three-step change of the acoustic power for IOP measurement as described above, to include an automatic study of ocular rigidity by applying programmable and externally synchronized step-wise changes in the ultrasonic pressure used will lead to further inestimable advances in the accuracy of IOP determination. Other problems relating to variations of the tensile strength of the cornea and the radius of curvature (ROC) from eye to eye can also be corrected for in this way. Consider, for instance, the possibilities for reducing the effect of variation of the ROC on the IOP reading, without preliminary measurement of the ROC value; it requires the instrument be calibrated only once using an appropriate model eye with known ROC ($R_0$), variable controllable pressure ($P_{in}$) and known (or negligible low) rigidity of the surface. To accomplish this the "self-calibration" and "external synchronization" features described above must be disabled. Then the first shot with the acoustic pressure value of $P_{rp1}$ will produce some deformation corresponding to the IOP reading $P_{in1}$. The second, more powerful shot $P_{rp2}$ will give a reading $P_{in2}$. Since the deformation is proportional to the acoustic pressure in a wide range of the $P_{rp}$ values, the dimensionless coefficient $K_0=(P_{in2}-P_{in1})/(P_{rp2}-P_{rp1})$ can be treated as a corrective instrument-constant for the standard ROC=$R_0$ value. Exactly the same procedure has to be used for the instrument calibration intended for individual use. If now the similar set of measurements is done on the real eye having R≠$R_0$, than the coefficient K will be smaller (if R>$R_0$) or larger (if R<$R_0$) than $K_0$ and the ROC-correction of the measured IOP can be written as IOP$_{corr}$=IOP$_{read}$($K_0$/K). The acoustic pressure values $P_{rp1}$ and $P_{rp2}$ during the measurement on the real eye should be chosen reasonably low to eliminate a non-linear response of the corneal tissue to the degree of deformation, i.e., to keep it in the linear region. It is important that although the deformation is inversely proportional to the ROC and therefore is a non-linear function of ROC, it can be approximated by a linear function with a negative slope without loss of accuracy in the relatively narrow range of the ROC variation of about 10%.

The tonometer of the present invention can have several different configurations depending on specific needs such as individual, clinical or advanced usage.

A tonometer for individual use is disclosed in FIG. 6A. Here the tonometer comprises an electronic block (not shown), transducer assembly 68 (shown in more detail in FIG. 6B), and the goggle-type adapter 66 which allows a steady, reproducible and convenient fitting on the patient's head 64, reducing to a minimum (or eliminating completely) the need for correction of the adjustments before each measurement if the very first adjustment has been done properly. It also eliminates any specific requirements regarding the patient's head orientation as well as fixation during the measurement. The goggle-type adapter can be made on the basis of the one of any commercially available safety goggles with an enforced frame 84. As shown in FIG. 6A, it has two identical holders 74 of the transducer assembly 68, and, if all preliminary adjustments are made for both sides, it allows the measurement of the IOP on both eyes. The patient is required only to move the transducer assembly from one holder to the other. The design of the adapter 66 allows all necessary degrees of freedom of the holders 74 to accomplish an individualized fitting of the instrument in accordance with the size and shape of the patient's head and face and the distance between the eyes. A rectangular lug 70 in the middle of the upper part of the frame 84 holds the horizontally inserted cylindrical shaft relative to which the bushings 78 can slide and rotate. Bushings 78 are connected to the holders 74 allowing adjustment of the distance between them corresponding to the patient's interpupilary distance as well as the parallelism of the joining pins 76 to the visual axis when the eye is fixated on a fixation light (this should be done with the transducer assembly 68 in place). These adjustments need to be made only once for each individual. The frame 40 of transducer assembly 68 has two symmetrically positioned rectangular joining grooves 88 (FIG. 6B) which allow the assembly to slide along the pins 76 for an adjustment of the proper eye-instrument distance. The proper distance for each side can be fixed by corresponding stops (not shown) placed on one of the two joining pins 76 and likely will not require readjustments before subsequent measurements. Inside the frame of the holders 74 there are two plates (not shown) which can move in the two perpendicular directions. The joining pins 76 are connected to the outer plates, and the transducer assembly 68, when inserted in place, can be properly aligned using thumb-nuts 72 and 82 and following the simple procedure described previously. The frames of holders 74, as well as both plates moving inside them, have rectangular openings sufficient to allow an ultrasonic beam to freely reach the eye as well as the receiver 52 after reflection. These openings also allow all indicator lights (42 in FIG. 1 and 80 in FIG. 6B) to be easily observable by the patient for fixation and alignment purposes. This goggle-type embodiment of the tonometer of the present invention is expected to be particularly easy to use by untrained people upon their own eyes.

The transducer assembly 68 is shown in FIG. 6B. The frame 40 with the joining grooves 88 provides a coaxial positioning of the transmitter 54 and the receiver 52 from the opposite sides of the reflecting surfaces 22. The receiver is shielded from any possible sound-type interference by a chamber 94 which completely suppresses cross-talk. It can also be provided with a collimator 90 to enhance the accuracy of the alignment (refer to FIGS. 3A and 3B). The path of the ultrasonic beam from the transmitter to the cornea 18 of the eye 16 (schematically represented by a hemisphere) and then to the receiver is designated by the phantom arrowhead lines 20, 24, 26, and 28. The two cables from the electronic block (not shown) are attached to the coaxial connectors 38 and 46. A cylindrical hole 44 (see also FIG. 1) provides a path for the light from the LED 42 (FIG. 1) which is used as an alignment indicator and as a fixating light. LED's 80 are the three indicators used for the distance adjustment. The light-type adjustment indicators can be replaced by sound-type ones which will simplify the transducer assembly by reducing the number of cables between it and the electronic block.

An alternative coaxial embodiment of the transducer assembly is shown in FIG. 6C. It has the same transmitter 54 inserted into a housing 100 with a concave surface at the end directed to the eye with the PVDF-type annular receiver 106 and 4-segment alignment sensor 102 glued on it. A central hole allows an incident beam 20 to reach eye 16. Any misalignment of the assembly relative to the apex of the cornea will produce displacement of the reflected beam 104 from the center, clearly indicated by four LEDs 80 related to the four sensors 102. A rigid cone 108 eliminates cross-talk. All necessary electronics for PVDF sensors can be placed into a compartment 98 with a connector 96. The transducer assembly of FIG. 6C is sufficiently compact allowing easy adjustments and can also be well suited for individual use.

For clinical use of the tonometer for patients, including for screening purposes, a conventional arrangement having a regular patient's head support and chin rest will be the most suitable. The transducer assembly can be moved to provide necessary adjustments in the x, y, and z directions using a mechanical joystick-type control mechanism. The same alignment and the distance control indicators should be placed on the operator's side as well to provide verification of alignment.

For further advanced use of the tonometer of this invention two additional sensors can be used, one for the acoustic pressure control and another one for an external synchronization with some physiological event, for instance, with the pulse beats. A disc-shaped ultrasonic pressure sensor 92, having diameter slightly larger than the beam diameter, made from PVDF film is shown in FIG. 6B. It is glued to the reflecting surface 22 and actually becomes a part of it. The high electrical impedance of the PVDF material requires a matching preamplifier in the close proximity to sensor 92 which can be placed inside frame 40 and connected to the electronic block by a cable. Both instrument configurations discussed above can be used depending on the particular application. In a goggle-type instrument configuration, the pulse beat sensor 86, if used as a part of the instrument, should be placed in the goggle area adjacent to the temporal artery as shown in FIG. 6A. In a case of the PVDF-type pulse beat sensor mentioned, a preamplifier needs to be placed nearby.

The goggle-type configuration allows simultaneous measurement of the IOP on both eyes if two transducer assemblies 68 and two-channel electronics are provided. This configuration in conjunction with the proposed method also allows sophisticated IOP measurements which were not possible before, including stress-type tests to study the IOP behavior on the moving or otherwise loaded patient.

This instrument can be provided either with a microprocessor for data collection and processing (in any of several modes of operation) or with an I/O interface allowing two-way communication with a computer equipped with appropriate software capable of handling the methods described herein.

We claim:

1. A single-beam, tone burst, non-contact, ultrasonic tonometer for measuring the intraocular pressure of an eye, comprising:

(a) ultrasonic means for generating a single ultrasonic beam and projecting it onto the eye and for detection and measurement of the beam reflected off the eye;

(b) means for measuring the distance to the eye based on the reflection of said ultrasonic beam off the eye including a means for adjusting said distance;

(c) means for aligning said tonometer with the eye based on the reflection of said ultrasonic beam off the eye; and (d) means for measuring and displaying the intraocular pressure by causing a deformation of the eye with the incident acoustic pressure from a tone burst of said ultrasonic beam and by assessing the deformation with the measured phase shift change in the ultrasonic beam reflected off the eye.

2. The tonometer of claim 1 further including means for positioning the tonometer device on a patient's head.

3. The tonometer of claim 2 wherein said means for positioning of said tonometer is a goggle-type device.

4. A single-beam, tone burst, non-contact, ultrasonic tonometer for measuring the intraocular pressure of an eye, comprising:

(a) ultrasonic means for generating a single ultrasonic beam and projecting it onto the eye and for detection and measurement of the beam reflected off the eye;

(b) means for measuring the distance to the eye based on the reflection of said ultrasonic beam off the eye including a means for adjusting said distance;

(c) means for aligning of said tonometer with the eye based on the reflection of said ultrasonic beam off the eye;

(d) ultrasonic means for absolute calibration of said tonometer;

(e) means for measuring and displaying the intraocular pressure by causing a small deformation of the eye with the incident acoustic pressure from a tone burst of said ultrasonic beam and by assessing the deformation with the measured phase shift change in the ultrasonic beam reflected off the eye;

(f) means for external synchronization of the measuring event with a physiological event; and (g) means for step-wise increase of the acoustic pressure produced by the tone burst of said ultrasonic beam in one measuring cycle for obtaining comparative intraocular pressure readings.

5. The tonometer of claim 4 wherein said ultrasonic means of (a) further including an ultrasonic transmitter and receiver separated by two adjacent flat, rigid surfaces oriented such that the incident ultrasonic beam from said transmitter reaching one of said surfaces is redirected onto the eye and the beam reflected off the eye is redirected to said receiver by said second surface.

6. The tonometer of claim 4 wherein the ultrasonic means of (d) further including means for acoustic pressure measurements comprising ferroelectric polymer film attached to one of the said rigid surfaces facing said transmitter such that it is an integral part of said rigid surface and an acoustic pressure sensor simultaneously.

7. The tonometer of claim 4 wherein means for external synchronization further including means for generating a signal corresponding to the pulse of heart beats or respiratory activity.

8. The tonometer of claim 7 wherein means for external synchronization further include an electronic means for allowing programmable time delay between a synchronizing signal and the moment of measurement.

9. The tonometer of claim 4 wherein means for step-wise increase of the acoustic pressure in one measuring cycle further include an electronic means for allowing programmable and externally synchronized change of the acoustic pressure directed onto the eye in one measuring cycle.

10. A method of measuring the intraocular pressure of an eye, comprising the steps of:

(a) projecting a continuous low power single ultrasonic beam onto the eye to track an initial phase shift value between an incident ultrasonic beam and the beam reflected off the non-deformed eye;

(b) powering up the incident beam for a short period of time to produce a tone burst carrying a predetermined acoustic pressure capable of causing a deformation of the eye and of measuring directly an incremental change in the initial phase shift caused by said deformation of the eye; and (c) determining the intraocular pressures from the phase increments using previously obtained instrument calibrations.

11. The method of measuring the intraocular pressure of the eye of claim 10 further including measuring eye-to-instrument distance and alignment of the incident beam with the surface of the eye using the beam reflected off the eye.

12. A method of measuring the intraocular pressure of an eye, comprising the steps of:

(a) projecting a continuous low power single ultrasonic beam onto the eye to track the initial phase shift value between an incident ultrasonic beam and the beam reflected off the non-deformed eye;

(b) powering up the incident ultrasonic beam for a short period of time producing a tone burst carrying an acoustic pressure capable of producing a deformation of the eye and measuring directly an incremental change in the initial phase shift in the reflected ultrasonic beam, this change being directly related to said deformation;

(c) measuring the acoustic pressure produced by the powered up ultrasonic tone burst projected onto the eye; and (d) obtaining an accurate intraocular pressure reading by autocorrecting the intraocular pressure corresponding to the phase increment with the use of the simultaneously measured actual acoustic pressure.

13. The method of measuring the intraocular pressure of the eye of claim 12 wherein the step (b) of powering up the incident beam further includes external synchronization of the powering-up moment allowing programmable and reproducible measurements coinciding with or following any synchronizing event with a programmable predetermined delay.

14. The method of measuring the intraocular pressure of the eye of claim 12 wherein the step (b) of powering up the incident beam further includes several consecutive powering-ups with step-wise increasing acoustic power allowing comparative measurements that help exclude undesirable effects on the intraocular pressure by eye characteristics such as corneal and scleral rigidities.

15. The method of measuring the intraocular pressure of the eye of claim 12 wherein the step (d) of obtaining the intraocular pressure reading further includes measuring the intraocular pressure response on the patient subjected to movements or other stress-loads.

16. The method of measuring the intraocular pressure of the eye of claim 15 wherein measurement is carried out on both eyes simultaneously.

* * * * *